US006941170B1

(12) United States Patent
Lu

(10) Patent No.: US 6,941,170 B1
(45) Date of Patent: Sep. 6, 2005

(54) DYNAMIC ADJUSTMENT OF OVERDRIVE PACING RATE BASED ON SENSOR INDICATED RATE

(75) Inventor: Richard Lu, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 674 days.

(21) Appl. No.: 09/963,205

(22) Filed: Sep. 25, 2001

(51) Int. Cl.⁷ ............................................... A61N 1/18
(52) U.S. Cl. .......................................... 607/14; 607/19
(58) Field of Search .............................. 607/18–20, 9, 607/17, 14

(56) References Cited

U.S. PATENT DOCUMENTS

| 4,712,555 | A | 12/1987 | Thornander et al. | 128/419 PG |
|---|---|---|---|---|
| 4,940,052 | A | 7/1990 | Mann et al. | 128/419 PG |
| 4,944,298 | A | 7/1990 | Sholder | 128/419 PG |
| 5,466,254 | A | 11/1995 | Helland | 607/123 |
| 5,476,483 | A | 12/1995 | Bornzin et al. | 607/17 |
| 6,058,328 | A | 5/2000 | Levine et al. | 607/14 |
| 6,574,507 | B1 * | 6/2003 | Bonnet | 607/20 |

* cited by examiner

Primary Examiner—Mark Bockelman

(57) ABSTRACT

An implantable cardiac stimulation device controls dynamic atrial overdrive pacing based, in part, on sensor indicated rate. In one example, the stimulation device adjusts an overdrive pacing rate based on the sensor indicated rate by periodically decreasing the overdrive pacing rate by a programmed rate decrement whenever a difference between the current overdrive pacing rate and the sensor indicated rate falls outside predetermined acceptable range while the sensor indicated rate is decreasing. The overdrive pacing rate is decreased in this manner until a) the overdrive pacing rate falls below the base rate, rest rate or the sensor indicated rate or until b) an event triggers an increase in the overdrive pacing rate, such as the appearance of intrinsic breakthrough heart beats. The overdrive pacing rate is not decreased if the sensor indicated rate is increasing or stable. With this process, the overdrive pacing rate is controlled to typically remain slightly above the intrinsic rate without being constrained by a preprogrammed number of pacing cycles. Hence, the overdrive pacing rate can be made to closely track the intrinsic rate regardless of whether the intrinsic rate is changing rapidly or is fairly stable.

41 Claims, 8 Drawing Sheets

US 6,941,170 B1

DYNAMIC ADJUSTMENT OF OVERDRIVE PACING RATE BASED ON SENSOR INDICATED RATE

FIELD OF THE INVENTION

The invention generally relates to implantable cardiac stimulation devices such as pacemakers or implantable cardioverter defibrillators (ICDs), and in particular, to techniques for overdrive pacing heart tissue to prevent arrhythmias.

BACKGROUND OF THE INVENTION

An arrhythmia is an abnormal heart rhythm. One example of an arrhythmia is bradycardia wherein the heart beats at an abnormally slow rate or wherein significant pauses occur between consecutive beats. Other examples of arrhythmias include tachyarrhythmias wherein the heart beats at an abnormally fast rate. With atrial tachycardia, the atria of the heart beat abnormally fast. With ventricular tachycardia, the ventricles of the heart beat abnormally fast. Though often unpleasant for the patient, an atrial tachycardia is typically not fatal. However, atrial fibrillation can cause stroke and other symptoms. Also, ventricular tachycardia can trigger ventricular fibrillation wherein the heart beats chaotically resulting in little or no net flow of blood from the heart to the brain and other organs. Ventricular tachycardia and ventricular fibrillation, if not terminated, are fatal. Hence, it is highly desirable to prevent or terminate arrhythmias, particularly ventricular tachycardias.

One technique for preventing arrhythmias is to overdrive pace the heart wherein an implantable cardiac stimulation device, such as a pacemaker or implantable cardioverter defibrillator (ICD), applies electrical pacing pulses to the heart at a rate somewhat faster than the intrinsic heart rate of the patient having a normal sinus rhythm. For bradycardia, the cardiac stimulation device may be programmed to pace the heart at a rate of 60 to 80 pulses per minute (ppm) to thereby prevent the heart from beating too slow and to eliminate any long pauses between heartbeats. To prevent tachyarrhythmias from occurring, the cardiac stimulation device paces the heart at a rate slightly faster than the intrinsic heart rate of the patient. In other words, overdrive pacing is applied and maintained in an effort to prevent an actual tachycardia from arising.

One particular technique is described in U.S. patent application Ser. No. 09/471,788 entitled "Improved Method for Establishing Pacing Rate During Dynamic Atrial Overdrive Pacing" by Joe Florio et al. filed Dec. 23, 1999. In that technique, the stimulation device monitors the heart of the patient and, if two consecutive intrinsic heartbeats are detected (or two intrinsic beats are detected within a predetermined number of cycles such as within the last sixteen cycles), overdrive pacing is automatically triggered. The overdrive pacing rate is calculated based on the heart rate detected at the time overdrive pacing is triggered and is typically 5 to 10 ppm higher than the intrinsic rate, i.e. an overdrive pacing rate increment of 5 to 10 bpm is added to the detected intrinsic rate. The intrinsic heart rate may be determined, for example, by calculating the time interval between the two consecutive intrinsic beats. The stimulation device then overdrive paces the heart at the selected overdrive pacing rate for a programmed number of overdrive events or "overdrive cycles". Thereafter, the stimulation device slowly decreases the overdrive pacing rate by a rate decrement specified by a programmed "recovery rate" until additional intrinsic beats are detected, then the device repeats the process to determine a new overdrive pacing rate and paces accordingly. If the heart rate is increasing quickly, such as may occur with an episode of tachycardia, the stimulation device may still detect intrinsic beats even while overdrive pacing is being applied. If so, the stimulation device immediately calculates a new higher overdrive pacing rate. If intrinsic beats are still detected, the overdrive pacing rate is increased again up to a maximum overdrive limit such as a preprogrammed maximum sensor rate.

Ultimately, the overdrive pacing rate will be increased to the point where it exceeds the intrinsic rate and hence no intrinsic beats will be detected. The pacing rate is eventually decreased using a programmed recovery rate until two or more consecutive intrinsic beats are again detected and the pacing rate is increased again. Assuming that overdrive pacing has succeeded in preventing tachycardia, the recovery rate will ensure that the pacing rate decreases slowly back down to a programmed base rate or sensor indicated rate. For example, if the base rate is programmed at 60 bpm, the heart will be paced at the base rate even if the recovery rate would otherwise cause the rate to decrease even further. Likewise, if an alternative base rate, such as the rest rate or circadian base rate is programmed, the pacing rate will not fall below those rates either.

It is believed that overdrive pacing is effective for at least some patients for preventing the onset of an actual tachycardia for the following reasons. A normal, healthy heart beats only in response to electrical pulses generated from a portion of the heart referred to as the sinus node. The sinus node pulses are conducted to the various atria and ventricles of the heart via certain, normal conduction pathways. In some patients, however, additional portions of the heart also generate electrical pulses referred to as "ectopic" pulses. Each pulse, whether a sinus node pulse or an ectopic pulse has a refractory period subsequent thereto during which time the heart tissue is not responsive to any electrical pulses. A combination of sinus pulses and ectopic pulses can result in a dispersion of the refractory periods, which, in turn, can trigger a tachycardia. By overdrive pacing the heart at a uniform rate, the likelihood of the occurrence of ectopic pulses is reduced and the refractory periods within the heart tissue are rendered uniform and periodic. Thus, the dispersion of refractory periods is reduced and tachycardias triggered thereby are substantially avoided.

Thus it is desirable within patients prone to tachyarrhythmias to ensure that most beats of the heart are paced beats, as any unpaced beats may be ectopic beats. A high percentage of paced beats can be achieved simply by establishing a high overdrive pacing rate. However, a high overdrive pacing rate has disadvantages as well. For example, a high overdrive pacing rate may be unpleasant to the patient, particularly if the artificially-induced heart rate is relatively high in comparison with the heart rate that would otherwise normally occur. A high heart rate may also cause possible damage to the heart or may possibly trigger more serious arrhythmias, such as a ventricular fibrillation. A high overdrive pacing rate may be especially problematic in patients suffering from heart failure, particularly if the heart failure is due to an impaired diastolic function. A high overdrive pacing rate may actually exacerbate heart failure in these patients. Also, a high overdrive pacing rate may be a problem in patients with coronary artery disease because increasing the heart rate decreases diastolic time and decreases perfusion, thus intensifying ischemia. Also, the need to apply overdrive pacing pulses operates to deplete a power supply of the implantable cardiac stimulation device, perhaps requiring frequent surgical replacement of the device.

The various overdrive pacing parameters (the overdrive pacing rate increment, the number of overdrive cycles, the recovery rate decrement) are programmed by a physician using an external programmer in an attempt to ensure that an optimal degree of overdrive pacing is achieved of typically 85% to 95%. Unfortunately, it is quite difficult for a physician to initially determine the parameters needed to achieve the desired degree of overdrive pacing within a particular patient. Instead, the physician typically sets the various control parameters of the stimulation device of the patient to default values and then programs the device to record the resulting degree of overdrive pacing as a function of heart rate. The patient is sent home and, weeks or months later, the patient returns to the physician for a follow-up session to permit the physician to review the recorded information and to determine whether the default parameters achieved the desired degree of overdrive pacing. If the degree of overdrive pacing is too low, perhaps only 50%, the physician typically increases the number of overdrive cycles or selects a more aggressive overdrive pacing rate increment. If the degree of overdrive pacing is too high, perhaps 100%, the physician may decrease the number of overdrive cycles or may select a lower overdrive pacing rate increment. The patient is again sent home and, weeks or months later, the patient again returns to the physician so that the physician can again review the recorded degree of overdrive pacing and, if needed, re-set the number of overdrive events or the overdrive pacing rate. This process is usually repeated several times over a period of months until a number of overdrive events and an overdrive pacing rate increment are identified that comes closest to achieving the desired degree of overdrive pacing. During this process the physician may also adjust any of the other parameters as well, such as the base rate, recovery rate etc.

Although the aforementioned technique is generally effective to control overdrive pacing, room for improvement remains. One particular area of concerns relates to the difficulty in programming an optimal number of overdrive events or cycles. Typically, the number of overdrive events is set to a value within a range 10–90 cycles. While the intrinsic heart rate of the patient is decreasing, a small number of cycles is preferred as that ensures that the overdrive pacing rate promptly decreases to the intrinsic rate to prevent unnecessary and prolonged overdrive pacing at a rate much higher than the intrinsic rate. However, while the intrinsic rate of the patient is generally stable or slowly increasing, a large number of cycles is preferred as that prevents frequent changes in the overdrive pacing rate, which can be an annoyance to the patient. As can be appreciated, if the number of overdrive cycles must be set by the physician to a single value that remains fixed until a subsequent follow-up session, optimal overdrive pacing may not always be achieved.

FIGS. 1 and 2 illustrate these problems. FIG. 1 shows an intrinsic rate 2 and a resulting overdrive pacing rate 3 wherein the intrinsic rate varies fairly quickly and the number of overdrive pacing cycles 4 is set fairly high. As can be seen, the overdrive pacing rate reacts fairly slowly to changes in the intrinsic heart rate, resulting in an overdrive pacing rate that is considerably higher than necessary at times. FIG. 2 shows an intrinsic rate 6 and a resulting overdrive pacing rate 7 wherein the intrinsic rate is fairly stable and the number of overdrive pacing cycles 8 is set fairly low. As can be seen, the overdrive pacing rate varies considerably even though the intrinsic rate is stable; resulting in frequent unwanted changes in heart rate.

Accordingly, it would be desirable to provide an improved overdrive pacing technique, which does not employ a fixed number of overdrive cycles, and it is to that end that the invention is primarily directed.

SUMMARY OF THE INVENTION

In accordance with the invention, a technique is provided for use within an implantable cardiac stimulation device for controlling overdrive pacing so as to eliminate the need for a fixed number of overdrive cycles. The technique is employed with an implantable cardiac stimulation device having a sense amplifier for receiving signals representative of electrical activity in the heart of a patient and a separate rate-responsive sensor for generating signals representative of a degree of activity of the patient, such as a physiological sensor. The stimulation device also has a pulse generator for generating pacing pulses for delivery to the heart of the patient and a control unit for controlling the pulse generator. In accordance with the invention, the control unit determines a sensor indicated rate based on signals received from the rate-responsive sensor, then controls overdrive pacing based on the sensor indicated rate and on the electrical heart signals received from the sense amplifier.

In an exemplary embodiment, the implantable device is a pacemaker or ICD and the rate-responsive sensor is a minute ventilation sensor. The control unit determines the sensor indicated rate based on minute ventilation values then controls the overdrive pacing rate by periodically decreasing a current overdrive pacing rate by a programmed rate decrement whenever a difference between the current overdrive pacing rate and the sensor indicated rate exceeds a fixed or programmed threshold value while the sensor indicated rate is decreasing. The overdrive pacing rate is decreased in this manner until a) the overdrive pacing rate falls below the base rate, rest rate or sensor indicated rate or until b) an event triggering an increase in the overdrive pacing rate is detected, such as one or more intrinsic breakthrough beats. The overdrive pacing rate is not decreased if the sensor indicated rate is increasing or stable.

In this manner, the overdrive pacing rate is controlled to typically remain slightly above the intrinsic heart rate without being constrained by a preprogrammed number of pacing cycles. In particular, the overdrive is controlled to typically remain slightly above the intrinsic rate regardless of whether the intrinsic rate is fairly stable or is increasing or decreasing rapidly.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Stimulation Device

Figure 3:
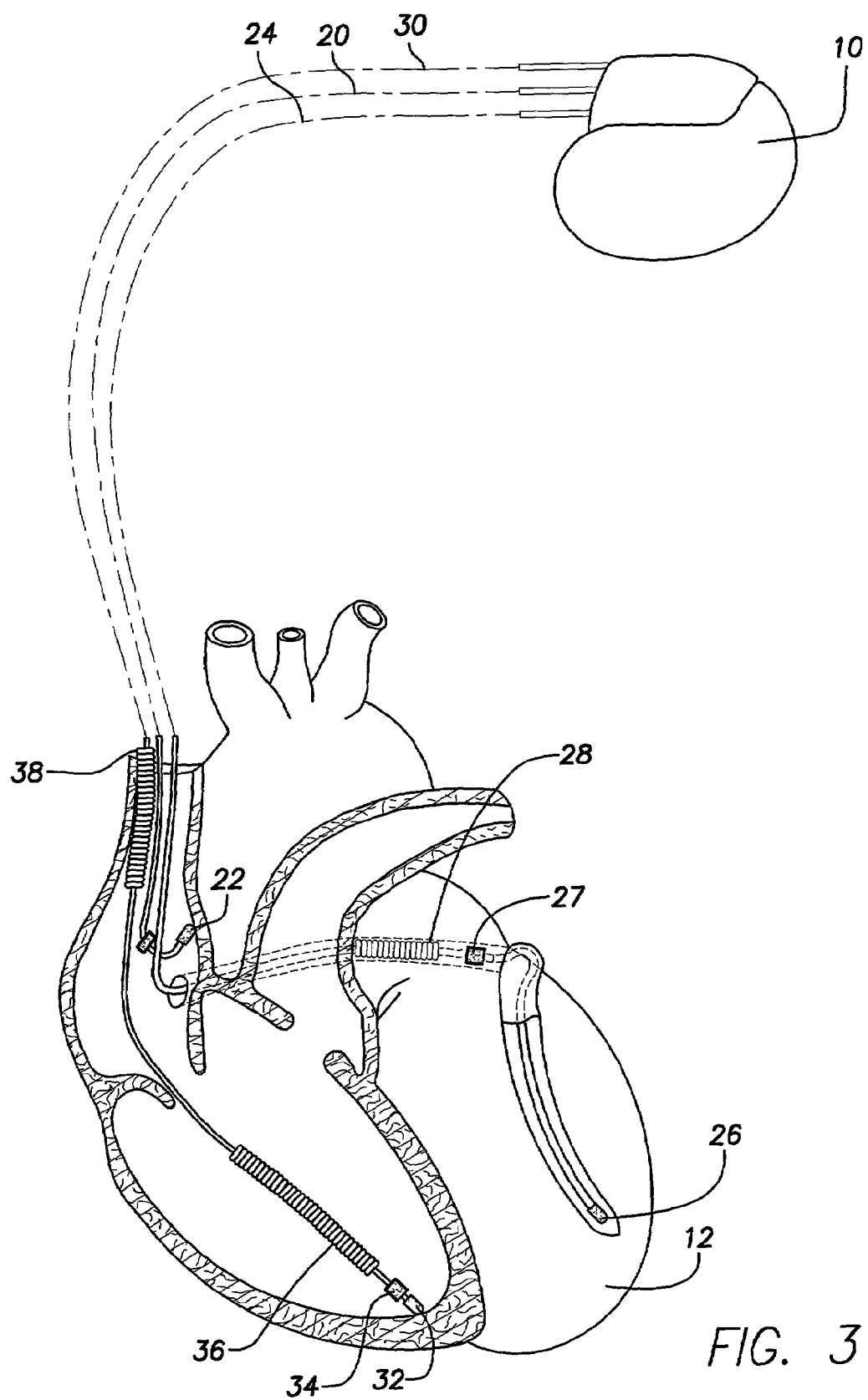
FIG. 3 is a simplified diagram illustrating an implantable stimulation device in electrical communication with at least three leads implanted into the heart of a patient for delivering multi-chamber stimulation and shock therapy and configured in accordance with the invention to perform overdrive pacing.

As shown in FIG. 3, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. Pat. No. 5,466,254, "Coronary Sinus Lead with Atrial Sensing Capability" (Helland), incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 4:
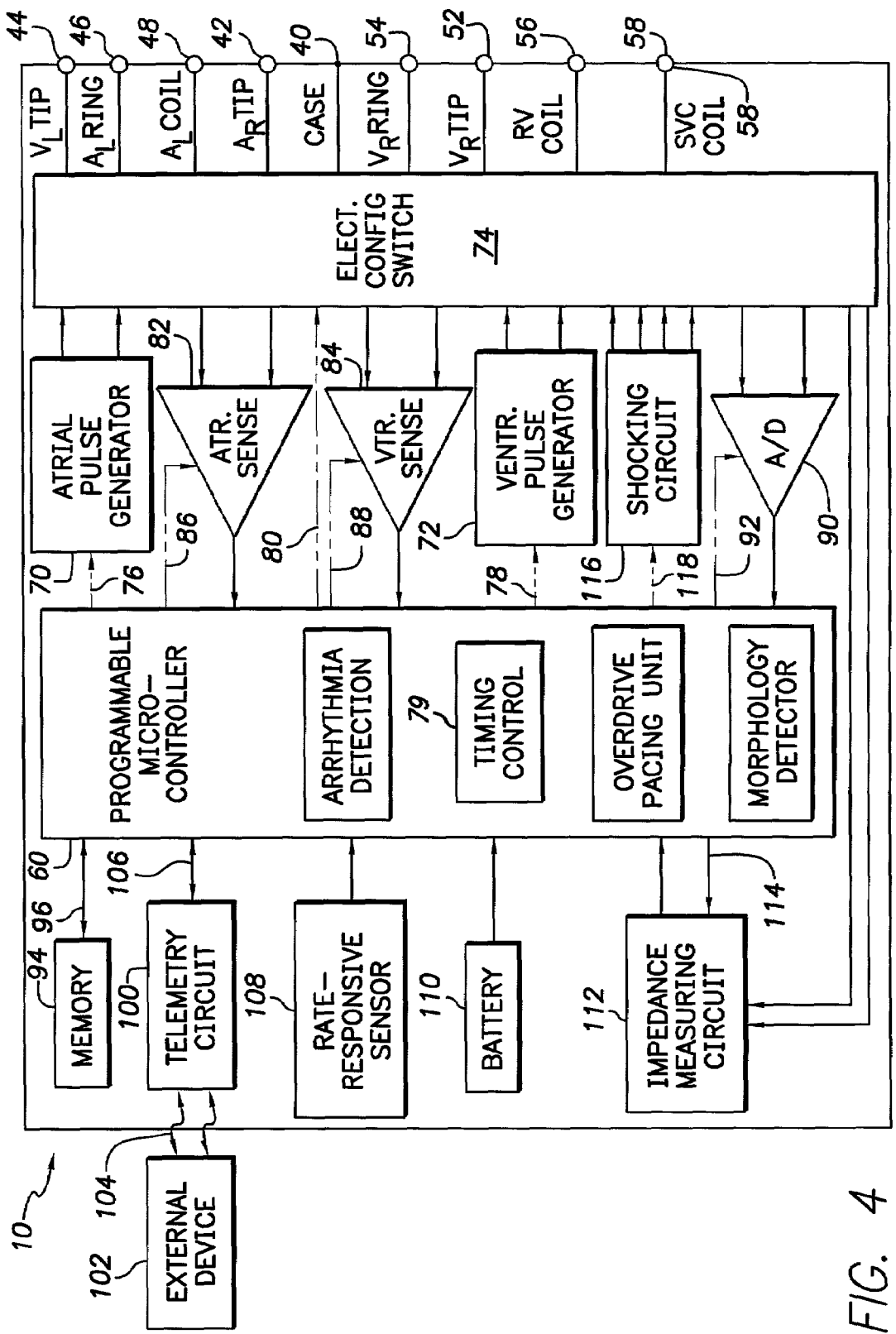
FIG. 4 is a functional block diagram of the implantable cardiac stimulation device of FIG. 3 illustrating basic elements of a stimulation device.

As illustrated in FIG. 4, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 4, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art. Representative types of control circuitry that may be used with the invention include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder).

As shown in FIG. 4, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

Stimulation device 10 further includes a rate-responsive sensor 108 used to adjust a pacing stimulation rate according to the exercise state or degree of activity of the patient. The rate-responsive sensor may be any sensor capable of generating a signal for use in performing rate-responsive pacing. Sensor 108 may be, for example, a physiological sensor for determining a physiological characteristic of the patient, such as a minute ventilation sensor or other sensors which sense the oxygen content of blood, respiration rate, pH of the blood, ventricular gradient, etc. Sensor 108 may be a sensor that generates values representative of the degree of exercise of the patient based on an analysis of electrical signals in the heart, such as a paced depolarization integral sensor. Sensor 108 may alternatively be configured to detect changes in cardiac output, changes in the physiological condition of the heart, or diurnal changes in activity (e.g., detecting sleep and wake states). Sensor 108 may be a physical activity sensor, such as an accelerometer or a piezoelectric crystal, which detects the motion of the patient. The physical activity sensor may be employed in conjunction with an "activity variance" sensor, which monitors the activity sensor diurnally to detect the low variance in the measurement corresponding to the sleep state. For a complete description of an activity variance sensor, see U.S. Pat. No. 5,476,483 (Bornzin et al.), issued Dec. 19, 1995, which patent is hereby incorporated by reference. While shown as being included within the stimulation device 10, it is to be understood that the rate-responsive sensor 108 may also be external to the stimulation device 10, yet still be implanted within or carried by the patient.

In general, any sensor (or combination of sensors) may be used which is capable of generating a parameter that corresponds to the exercise state or degree of activity of the patient. Two or more rate-responsive sensors may be employed in combination. The signal or signals generated by the sensors are processed by the microcontroller to determine a sensor indicated rate for the patient. As will be explained below, an overdrive pacing unit 103 of the microcontroller controls overdrive pacing based on the sensor indicated rate.

The stimulation device additionally includes a battery 110 that provides operating power to all of the circuits shown in FIG. 4. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 4, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Control of Overdrive Pacing Based on Sensor Indicated Rate

Figure 5:
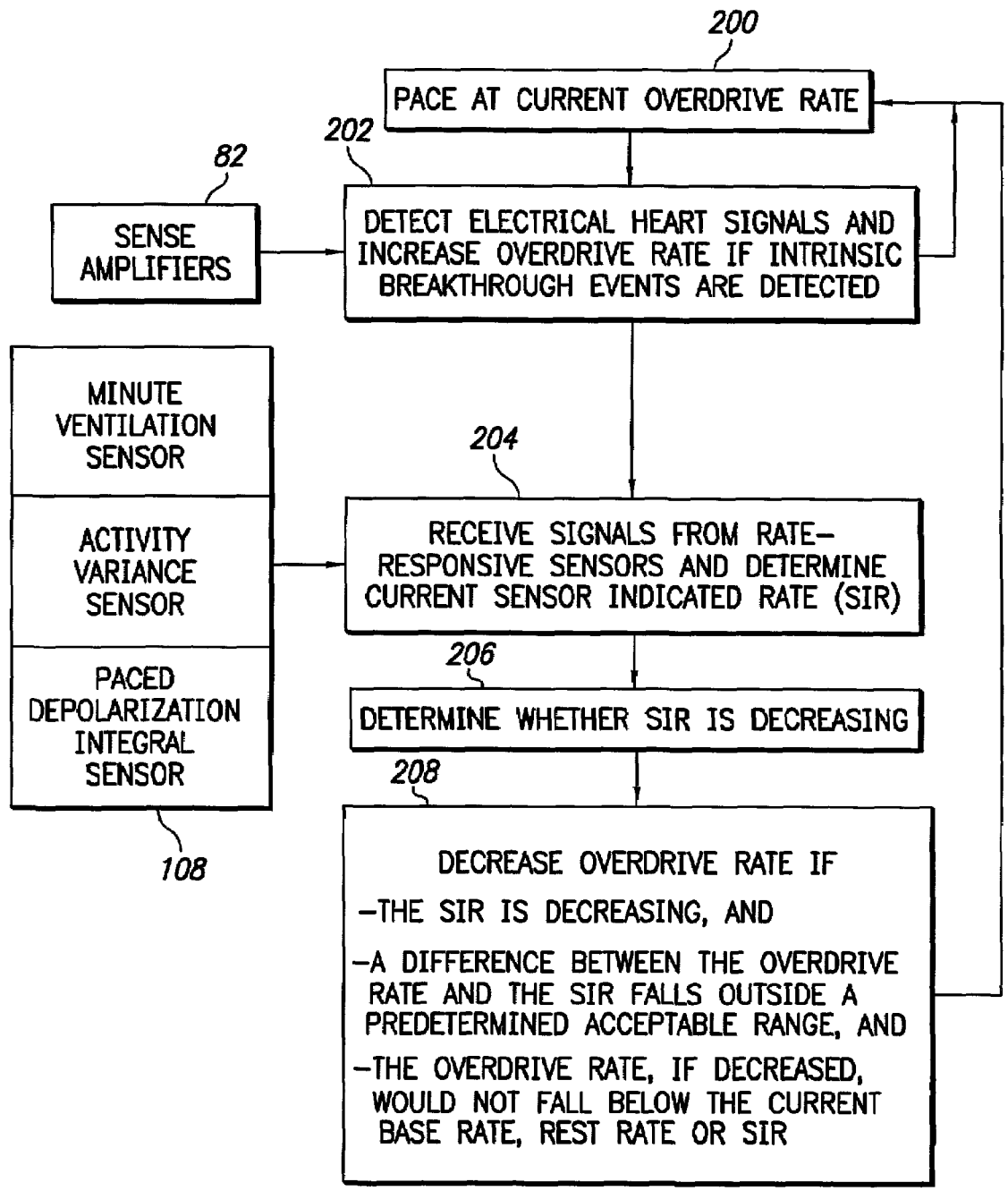
FIG. 5 is a high level flow chart providing an overview of the operation of an exemplary embodiment of the invention wherein the implantable stimulation device of FIGS. 3 and 4 automatically controls overdrive pacing based on sensor indicated rate.

Referring next to FIG. 5, a flow chart is shown describing an overview of the operation and novel features of stimulation device 10 as configured in accordance with the an embodiment of the invention. In this flow chart, and the other flow charts described herein, the various algorithmic steps are summarized in individual "blocks". Such blocks describe specific actions or decisions made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The stimulation device (FIG. 4) paces the heart at a previously determined overdrive pacing rate at step 200 while detecting electrical signals from the heart at step 202 using one or more sense amplifiers 82 and 84. If intrinsic breakthrough events are detected in the heart signals, the overdrive pacing rate is increased. Otherwise, the stimulation device receives signals at step 204 from one or more rate-responsive sensors 108 and determines a current sensor indicated rate. The rate-responsive sensor may include, for example, one more of a minute ventilation sensor, an activity sensor, and a paced depolarization integral sensor. If more than one sensor is used, the sensor indicated rate may be based on a combination of rates derived from the respective sensors. At step 206, the stimulation device determines whether the sensor indicated rate is currently decreasing. The overdrive pacing rate is decreased at step 208 if a) the sensor indicated rate is currently deceasing, b) a difference between the overdrive pacing rate and the sensor indicated rate falls outside a predetermined acceptable range, and c) the overdrive pacing rate, if decreased, would not fall below the current sensor indicated rate, base rate or rest rate. In this manner, the overdrive pacing rate is controlled to typically remain slightly above the intrinsic rate without being constrained by a preprogrammed number of pacing cycles. Hence, more responsive overdrive pacing typically may be achieved.

Figure 6:
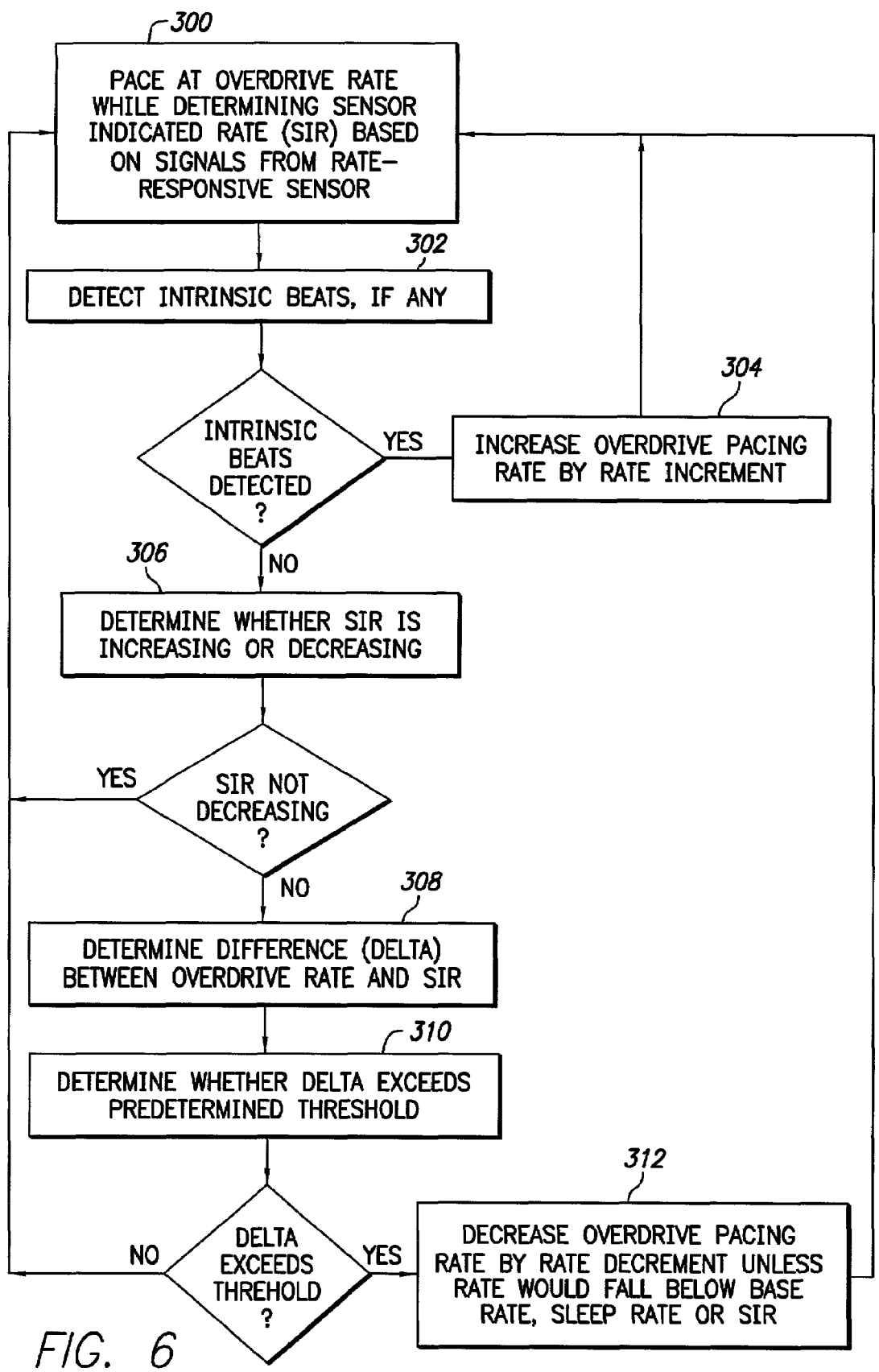
FIG. 6 is a detailed flow chart illustrating a specific exemplary method for controlling overdrive pacing based on sensor indicated rate in accordance with the overall method of FIG. 5.

Referring next to FIG. 6, a more detailed description of the method for controlling the overdrive pacing rate based on the sensor indicated rate will now be provided. Initially, at step 300, the stimulation device (FIG. 4) paces the heart at a previously determined overdrive pacing rate while determining the sensor indicated rate based on signals received from one or more rate-responsive sensors. If step 300 is being performed for the first time, the stimulation device uses a default rate as the initial overdrive pacing rate. Thereafter, the stimulation device uses an overdrive pacing rate calculated by overdrive pacing unit 103 (also FIG. 4) using the steps of FIG. 6. At step 302, the overdrive pacing unit determines whether any intrinsic beats have been detected and, if so, the overdrive pacing unit increases the overdrive pacing rate at step 304 and returns to step 300 to pace at the increased rate. In determining whether any intrinsic beats have been detected, the overdrive pacing unit may be programmed to determine whether a predetermined number of consecutive intrinsic beats (typically two beats) have been detected without any intervening paced beats. Alternatively, the overdrive pacing unit may be programmed to determine whether some number of intrinsic beats have been detected out of a predetermined number of total beats (for example, two intrinsic beats out of ten total beats). Still other techniques may be employed for triggering an increase in overdrive pacing rate and no attempt is made herein to describe all possible techniques. The sensor indicated rate is determined at step 300 using any appropriate determination technique and will depend upon the particular rate-responsive sensor or combination of sensors employed. As noted above, suitable rate-responsive sensors include a minute ventilation sensor, activity sensor, or the like. Typically, a table is provided within the stimulation device, which relates particular rate-responsive sensor output signal values to sensor indicated rate values. If two or more sensors are employed, the sensor indicated rate values derived from the various sensors may be combined to yield a single sensor indicated rate value. Also, although not shown in the figure, the overdrive rate is also increased whenever an increase in the sensor indicated rate would place the sensor indicated rate above the overdrive pacing rate. Hence, the sensor indicated rate will never exceed the overdrive pacing rate.

If no event is detected at step 302 that triggers an increase in overdrive pacing rate, then the overdrive pacing unit proceeds to step 306 to determine whether the sensor indicated rate is decreasing. This determination may be made by comparing the most recent sensor indicated rate value with the last previous sensor indicated rate value. Alternatively, the determination may be made by comparing the average of the last N number of sensor indicated rate values with the average of previous N number of sensor indicated rate values (where N is some predetermined number), so as to ensure that a single aberrant sensor indicated rate value does not unduly affect the overdrive pacing rate. Other more sophisticated statistical techniques may be employed for determining whether the sensor indicated rate is currently increasing or decreasing. The sensor indicated rate may be determined using any of the rate-responsive sensors mentioned above, such as a minute ventilation sensor, activity sensor, and the like, or some combination of rate-responsive sensors. In any case, if the sensor indicated rate is not decreasing (i.e. it is increasing or is stable), processing simply returns to step 300 for continued pacing at the current overdrive pacing rate. However, if the sensor indicated rate is decreasing, then the overdrive pacing unit instead performs steps 308 and 310 to calculate a difference (Delta) between the sensor indicated rate and the current overdrive pacing rate and to determine whether the difference (Delta) exceeds a predetermined threshold value such as 20 ppm.

If the difference (Delta) exceeds the predetermined threshold value (i.e. Delta falls outside a predetermined acceptable range), then the overdrive pacing unit decreases the overdrive pacing rate at step 312 by a predetermined rate decrement unless the decreased overdrive pacing rate would fall below either the base rate, rest rate or the current sensor indicated rate. If the decreased overdrive pacing rate would fall below either the base rate, rest rate or the current sensor indicated rate, the overdrive pacing rate may remain the same or stay at the base rate, rest rate, or circadian rate. If the difference (Delta) does not exceed the predetermined threshold value, then the overdrive pacing rate instead remains the same. In either case, processing returns to step 300 for continued overdrive pacing (either using the new decreased rate or using the same overdrive pacing rate as before.) Steps 300–312 may be performed as frequently as possible, and typically once every heart cycle, to provide appropriate adjustments to the overdrive pacing rate.

Figure 1:
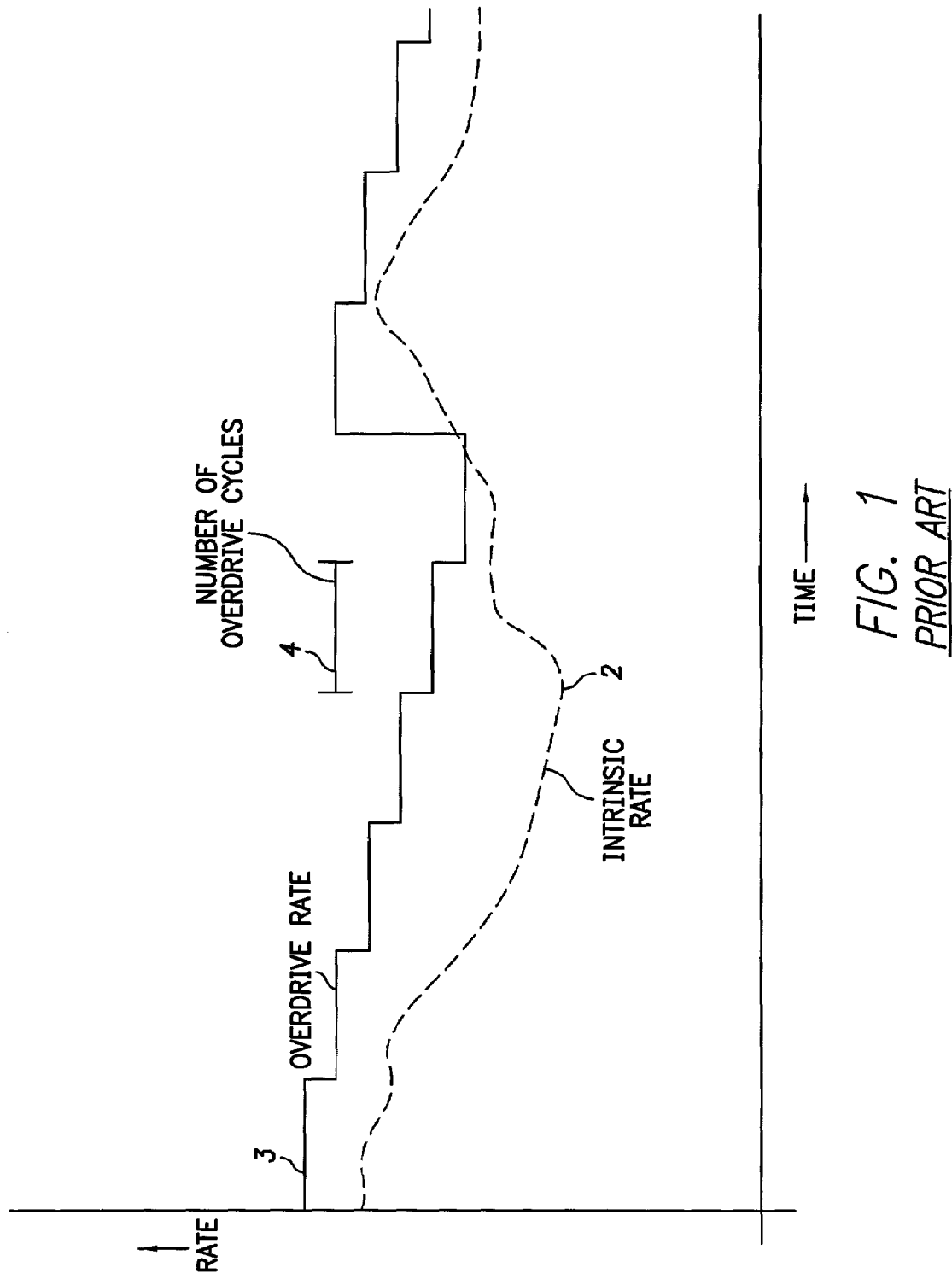
FIG. 1 is a graph illustrating an exemplary overdrive pacing rate achieved using conventional techniques when the intrinsic heart rate varies considerably.
Figure 7:
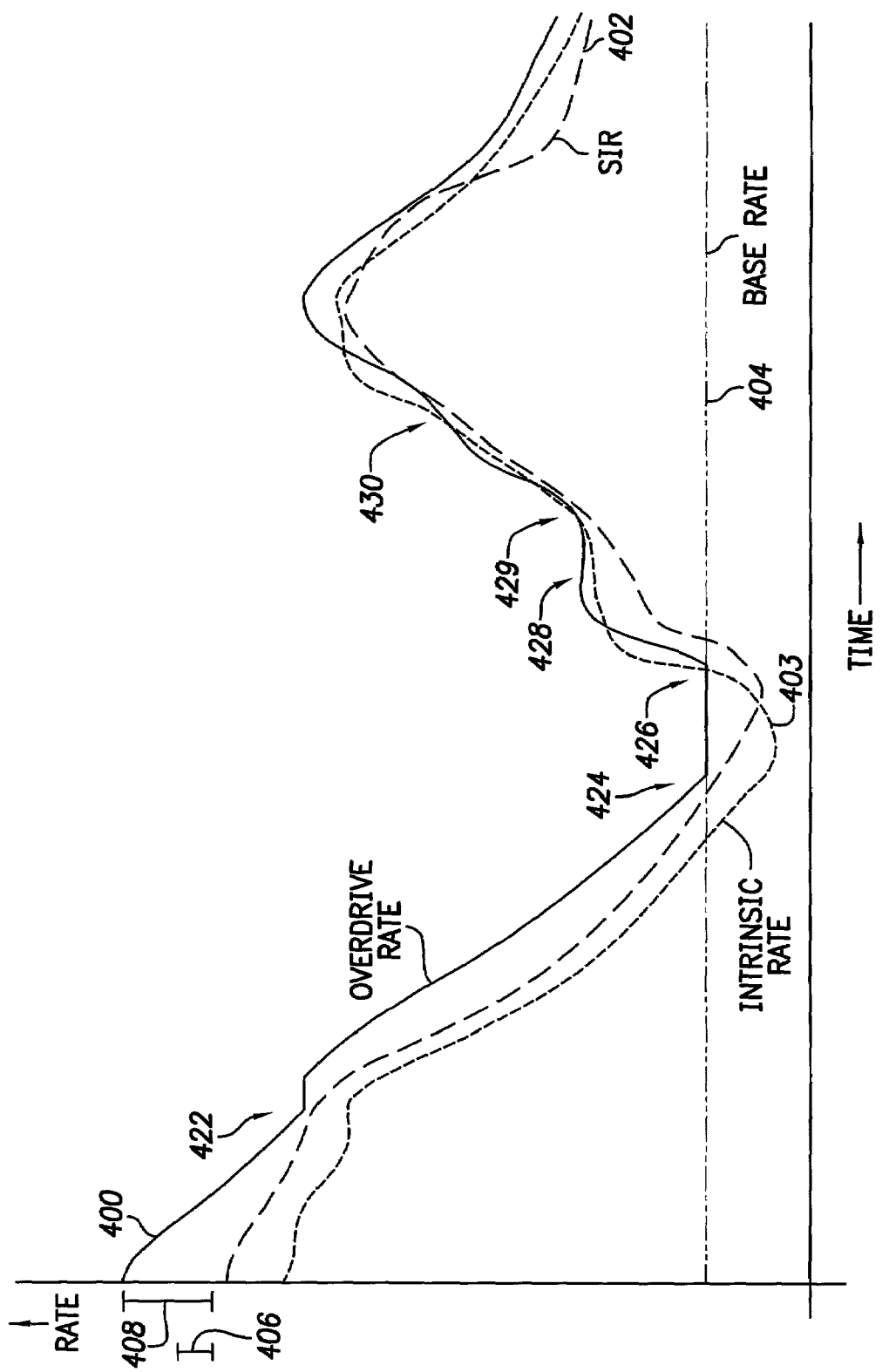
FIG. 7 is a graph illustrating an exemplary overdrive pacing rate achieved for the intrinsic heart rate shown in FIG. 1 when using the method of FIG. 5.

FIG. 7 is a graph illustrating adjustments made to the overdrive pacing rate using the methods described above for an exemplary intrinsic heart rate (also shown in FIG. 1). More specifically, the graph shows an overdrive pacing rate 400 (in solid lines), a sensor indicated rate 402 (in long dashed lines), an intrinsic rate 403 (in short dashed lines), and a preprogrammed base rate 404 (in broken dashed lines). The graphs are rate as a function of time, both scaled in arbitrary units. The difference between the overdrive pacing rate and the sensor indicated rate is an amount Delta 408, which varies with time as the overdrive pacing rate and the sensor indicated rate change. (The Delta value shown in the figure is representative of the difference between overdrive pacing rate and sensor indicated rate only at the starting time of the graph. Thereafter, the Delta value changes continuously as a function of time as a result of changes in the overdrive pacing rate and sensor indicated rate.) As noted above, the overdrive pacing rate is decreased if the amount Delta exceeds a Threshold value, identified in the graph as 406.

Initially, Delta 408 exceeds Threshold 406 and so the overdrive pacing rate is decreased until a point in time 422 when a further decrease would cause the overdrive pacing rate to fall below the sensor indicated rate. Thereafter, for a short period of time, the overdrive pacing rate remains constant. Then, once the sensor indicated rate has dropped so that Delta again exceeds the Threshold, the overdrive pacing rate is decreased to track the sensor indicated rate until further decreases would cause the overdrive pacing rate to fall below the base rate at time 424. The overdrive pacing rate then remains at the base rate until an intrinsic breakthrough event occurs at time 426 causing an increase in the overdrive pacing rate. The overdrive pacing rate remains stable during a time period 428 while the overdrive pacing rate continues to exceed the intrinsic rate. The overdrive pacing rate is increased again when intrinsic breakthrough events 429 and 430 are detected. Eventually, the sensor indicated rate and intrinsic rate begin to decrease triggering corresponding decreases in the overdrive pacing rate.

Figure 2:
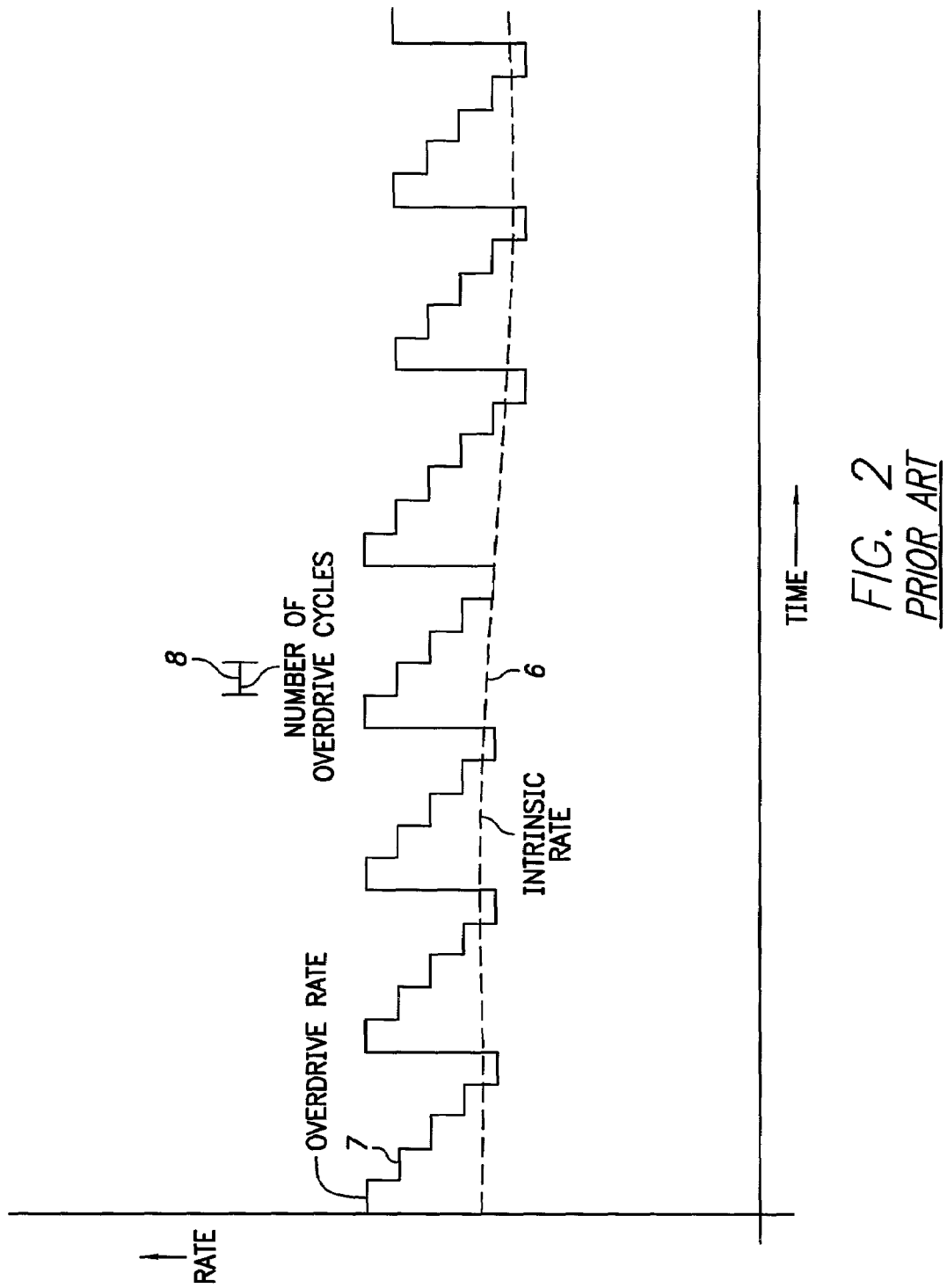
FIG. 2 is a graph illustrating an exemplary overdrive pacing rate achieved using conventional techniques when the intrinsic heart rate is fairly stable.
Figure 8:
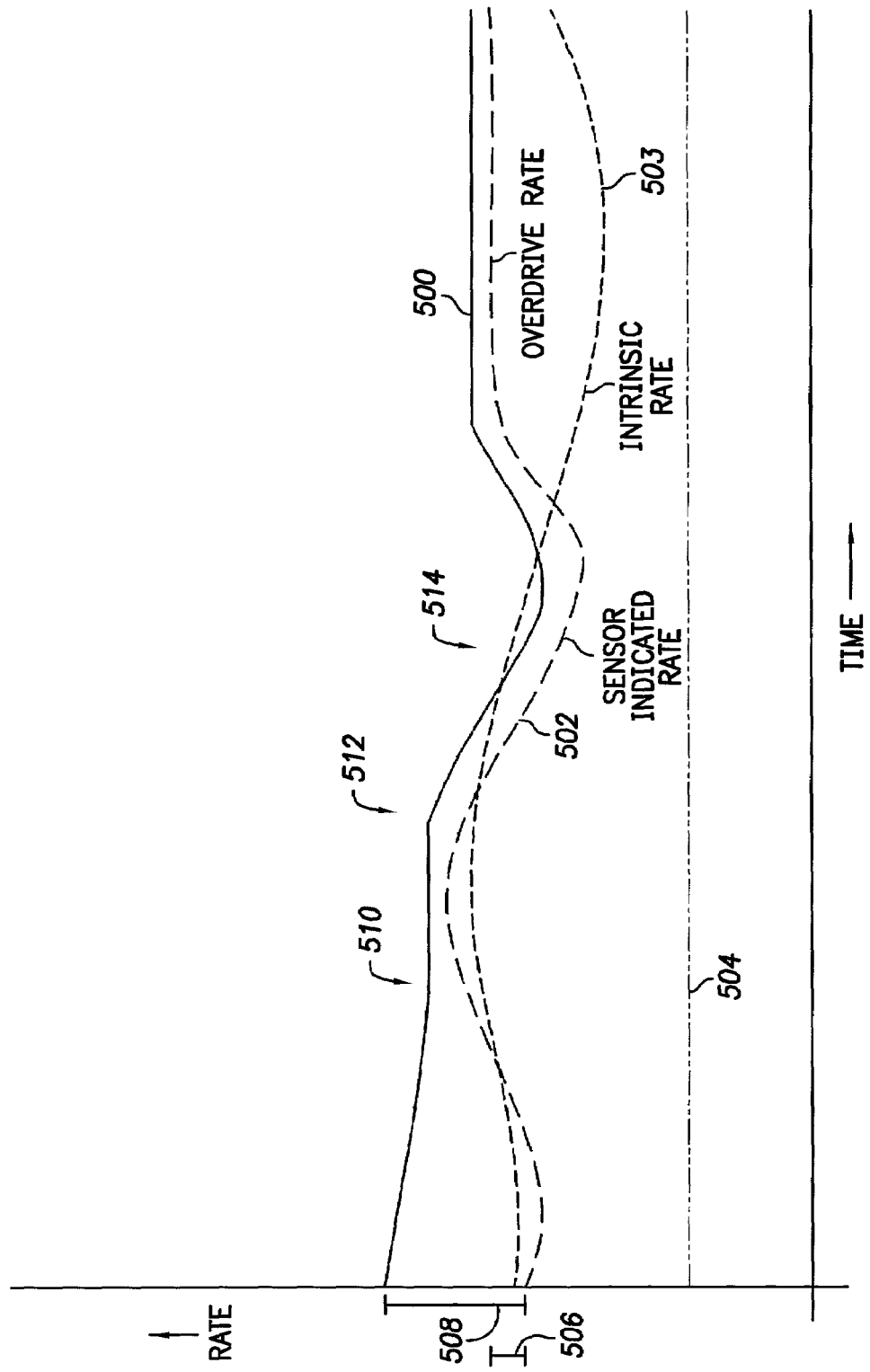
FIG. 8 is a graph illustrating an exemplary overdrive pacing rate achieved for the intrinsic heart rate shown in FIG. 2 when using the method of FIG. 5.

FIG. 8 is a graph illustrating the control of the overdrive pacing rate for the intrinsic heart rate of FIG. 2. The graph shows an overdrive pacing rate 500, a sensor indicated rate 502, an intrinsic rate 503, and a preprogrammed base rate 504. The graph also illustrates a Threshold value 506 and a Delta value 508, the later calculated based on the overdrive pacing rate and the intrinsic rate at the starting time of the graph. Initially, Delta exceeds the Threshold and so the overdrive pacing rate is decreased until a point in time 510 when further decreases are not performed because Delta remains below the Threshold. The overdrive pacing rate remains constant until the sensor indicated rate drops enough so that Delta again exceeds the Threshold at time 512. Then, the overdrive pacing rate is again decreased to track the sensor indicated rate until a breakthrough event triggers an increase in the overdrive pacing rate at time 514. Thereafter, the overdrive pacing rate remains constant because no further breakthrough events are detected and Delta remains below the Threshold value.

Within FIGS. 7 and 8, note that changes in the overdrive pacing rate are performed as often as the values for the intrinsic rate and sensor indicated rate are updated, typically every cycle (though less frequent updates may instead be used). Hence, the overdrive pacing rate can respond quickly to changes in intrinsic rate and can fairly closely track the intrinsic rate, remaining slightly above it at most times. Also, because the overdrive pacing rate can respond quickly to changes in intrinsic rate, increases in the overdrive pacing rate need not be as great as those typically employed in the prior art. Also note that the values of FIGS. 7 and 8 are exemplary values not derived from actual experimental data. The exemplary values have been chosen so as to help illustrate the techniques of the invention. By using the techniques of the invention, the overdrive pacing rate closely tracks the intrinsic heart rate, typically remaining slightly greater than the intrinsic rate and thereby providing optimal overdrive pacing without requiring the programming of a number of overdrive pacing cycles.

What have been described are various techniques for automatically and dynamically adjusting an overdrive pacing rate based on sensor indicated rate. The techniques may be exploited for either atrial or ventricular overdrive pacing. Also, although described primarily with reference to an example wherein the implanted device is a defibrillation/pacer, principles of the invention are applicable to other implanted cardiac stimulation devices as well such as pacemakers without defibrillation capability. The various functional components of the exemplary systems may be implemented using any appropriate technology including, for example, microprocessors running software programs or application specific integrated circuits (ASICS) executing hard-wired logic operations. The exemplary embodiments of the invention described herein are merely illustrative of the invention and should not be construed as limiting the scope of the invention.

What is claimed is:

1. In an implantable cardiac stimulation device comprising a sense amplifier that receives signals representative of electrical activity in the heart of a patient, a rate-responsive sensor that generates signals representative of a degree of activity of the patient, a pulse generator that generates overdrive pacing pulses that are delivered to the heart of the patient, and a control unit that controls the pulse generator, a method for overdrive pacing the heart to prevent tachycardia, the method comprising:
   receiving signals from the rate-responsive sensor representative of a degree of activity of the patient;
   determining a sensor indicated rate based on the signals received from the rate-responsive sensor;
   receiving signals from the sense amplifier representative of electrical activity in the heart of the patient; and
   adjusting a pulse generator overdrive pacing rate based on the sensor indicated rate and on the intrinsic heart signals to generate overdrive pacing pulses for delivery to the heart to prevent tachycardia, wherein the overdrive pacing rate is decreased when a significant decrease of sensor indicated rate is determined by the controller.

2. The method of claim 1 wherein adjusting the pulse generator to generate overdrive pacing pulses comprises:
   identifying a current overdrive pacing rate;
   determining a difference between the current overdrive pacing rate and the sensor indicated rate; and
   decreasing the current overdrive pacing rate by a programmed rate decrement if a difference between the current overdrive pacing rate and the sensor indicated rate exceeds a threshold value.

3. The method of claim 2 wherein decreasing the current overdrive pacing rate by a programmed rate decrement is repeated whenever the difference between the current overdrive pacing rate and the sensor indicated rate exceeds the threshold value until the overdrive pacing rate falls below a lower rate limit.

4. The method of claim 3 wherein the lower rate limit is a predetermined base rate or rest rate.

5. The method of claim 3 wherein the lower rate limit is the sensor indicated rate.

6. The method of claim 2 further comprising determining whether the sensor indicated rate is decreasing and wherein decreasing the current overdrive pacing rate by a programmed rate decrement is only performed if the sensor indicated rate is decreasing.

7. The method of claim 1 wherein adjusting the pulse generator to generate overdrive pacing pulses comprises:
   detecting any intrinsic heart beats arising during overdrive pacing based on the intrinsic heart signals received from sense amplifier; and
   increasing the current overdrive pacing rate by a predetermined rate increment whenever an intrinsic heart beat is detected.

8. The method of claim 1 wherein adjusting the pulse generator to generate overdrive pacing pulses comprises:
   detecting any intrinsic heart beats arising during overdrive pacing based on the intrinsic heart signals received from the sense amplifier; and
   increasing the current overdrive pacing rate by a predetermined rate increment if a predetermined number of intrinsic heart beats are detected within a predetermined search period.

9. The method of claim 8 wherein the predetermined number of intrinsic heart beats is two and the predetermined search period is the last sixteen cycles.

10. The method of claim 1 wherein the rate-responsive sensor comprises a plurality of individual sensors and wherein determining a sensor indicated heart rate comprises combining signals from the plurality of sensors.

11. The method of claim 1 wherein the rate-responsive sensor comprises a minute ventilation sensor and wherein determining a sensor indicated heart rate comprises detecting minute ventilation and determining the sensor indicated heart rate from the minute ventilation.

12. The method of claim 1 wherein the rate-responsive sensor comprises an activity sensor for generating signals representative of a degree of physical activity of the patient and wherein determining a sensor indicated heart rate comprises converting the degree of physical activity into the sensor indicated heart rate.

13. The method of claim 1 wherein the rate-responsive sensor comprises a paced depolarization integral sensor and wherein determining a sensor indicated heart rate comprises converting paced depolarization integral sensor values into the sensor indicated heart rate.

14. An implantable cardiac stimulation system to prevent tachycardia, comprising:
   means for receiving signals representative of electrical activity in the heart of the patient;
   means for generating signals representative of a degree of activity of the patient;
   means for generating overdrive pacing pulses for delivery to the heart of the patient;
   means for adjusting a pulse generator overdrive pacing rate to prevent tachycardia, the means for adjusting the pulse generator comprising determining a sensor indicated heart rate based on the signals received from the means for generating signals representative of a degree of activity of the patient and then adjusting an overdrive pacing rate based on the sensor indicated rate and on heart signals received from the means for receiving signals representative of electrical activity, wherein the overdrive pacing rate is decreased when a significant decrease of sensor indicated rate is determined by the controller.

15. The system of claim 14 wherein the means for adjusting the pulse generator comprises:
   means for identifying a current overdrive pacing rate;

means for determining a difference between the current overdrive pacing rate and the sensor indicated rate; and means for decreasing the current overdrive pacing rate by a programmed rate decrement if a difference between the current overdrive pacing rate and the sensor indicated rate exceeds a threshold value.

16. The system of claim 15 wherein the means for decreasing the current overdrive pacing rate by a programmed rate decrement decreases the current overdrive pacing rate whenever the difference between the current overdrive pacing rate and the sensor indicated rate is found to exceed the threshold value until the overdrive pacing rate falls below a lower rate limit.

17. The system of claim 16 wherein the lower rate limit used by the means for decreasing the overdrive pacing rate is a predetermined base rate or rest rate.

18. The system of claim 16 wherein the lower rate limit used by the means for decreasing the overdrive pacing rate is the sensor indicated rate.

19. The system of claim 15 further including means for determining whether the sensor indicated rate is decreasing and wherein the means for decreasing the current overdrive pacing rate is operative to decrease the overdrive pacing rate only if the sensor indicated rate is found to be decreasing.

20. The system of claim 14 wherein the means for adjusting the pulse generator to generate overdrive pacing pulses comprises:

means for detecting any intrinsic heart beats arising during overdrive pacing based on the heart signals received from sense amplifier; and means for increasing the current overdrive pacing rate by a predetermined rate increment whenever an intrinsic heart beat is detected.

21. The system of claim 14 wherein the means for adjusting the pulse generator to generate overdrive pacing pulses also comprises:

means for detecting any intrinsic heart beats arising during overdrive pacing based on the heart signals received from sense amplifier; and means for increasing the current overdrive pacing rate by a predetermined rate increment if a predetermined number of intrinsic heart beats are detected within a predetermined search period.

22. The system of claim 21 wherein the predetermined search period is a predetermined number of cycles.

23. The system of claim 14 wherein the means for generating signals representative of a degree of activity of the patient comprises a plurality of individual sensors.

24. The system of claim 14 wherein the means for generating signals representative of a degree of activity of the patient comprises means for detecting a physiological characteristic of the patient.

25. The system of claim 24 wherein the means for detecting a physiological characteristic of the patient comprises means for detecting minute ventilation.

26. The system of claim 14 wherein the means for generating signals representative of a degree of activity of the patient comprises means for generating signals representative of a degree of physical activity of the patient.

27. The system of claim 14 wherein the means for generating signals representative of a degree of activity of the patient comprises means for determining a paced depolarization integral signal.

28. An implantable cardiac stimulation system to prevent tachycardia, comprising:

a sense amplifier operative to receive signals representative of electrical activity in the heart of the patient;

a rate-responsive sensor operative to generate signals representative of a degree of activity of the patient;

a pulse generator operative to generate overdrive pacing pulses for delivery to the heart of the patient;

a control unit operative to adjust an overdrive pacing pulse rate to prevent tachycardia, the control unit operative to generate overdrive pacing pulses by determining a sensor indicated heart rate based on the signals received from the rate-responsive sensor and then controlling the pulse generator based on the sensor indicated rate and on heart signals received from the sense amplifier, wherein the overdrive pacing rate is decreased when a significant decrease of sensor indicated rate is determined by the controller.

29. The system of claim 28 wherein the control unit is operative to adjust the pulse generator by identifying a current overdrive pacing rate, determining a difference between the current overdrive pacing rate and the sensor indicated rate, and decreasing the current overdrive pacing rate by a programmed rate decrement if a difference between the current overdrive pacing rate and the sensor indicated rate exceeds a threshold value.

30. The system of claim 29 wherein the control unit is operative to decrease the current overdrive pacing rate whenever the difference between the current overdrive pacing rate and the sensor indicated rate is found to exceed the threshold value until the overdrive pacing rate falls below a lower rate limit.

31. The system of claim 30 wherein the lower rate limit used by the control unit is a predetermined base rate or rest rate.

32. The system of claim 30 wherein the lower rate limit used by the control unit is the sensor indicated rate.

33. The system of claim 29 wherein the control unit is further operative to determine whether the sensor indicated rate is decreasing and the control unit decreases the overdrive pacing rate only if the sensor indicated rate is found to be decreasing.

34. The system of claim 28 wherein the control unit is also operative to detect any intrinsic heart beats arising during overdrive pacing based on the heart signals received from sense amplifier and to increase the current overdrive pacing rate by a predetermined rate increment whenever an intrinsic heart beat is detected.

35. The system of claim 28 wherein the control unit is operative to detect any intrinsic heart beats arising during overdrive pacing based on the heart signals received from sense amplifier and to increase the current overdrive pacing rate by a predetermined rate increment if a predetermined number of intrinsic heart beats are detected within a predetermined search period.

36. The system of claim 35 wherein the predetermined search period is a predetermined number of cycles.

37. The system of claim 28 wherein the rate-responsive sensor comprises a plurality of individual sensors.

38. The system of claim 28 wherein the rate-responsive sensor comprises physiological sensor.

39. The system of claim 38 wherein the physiologic sensor comprises a minute ventilation sensor.

40. The system of claim 28 wherein the rate-responsive sensor comprises a physical activity sensor.

41. The system of claim 28 wherein the rate-responsive sensor comprises a paced depolarization integral sensor.

* * * * *